(12) United States Patent
Bergman et al.

(10) Patent No.: US 8,163,856 B2
(45) Date of Patent: Apr. 24, 2012

(54) METHOD AND SYSTEM TO ADD HIGH SHEAR TO IMPROVE AN IONIC LIQUID CATALYZED CHEMICAL REACTION

(75) Inventors: Lee H. Bergman, Houston, TX (US);
Kenneth D. Hope, Kingwood, TX (US);
Elizabeth A. Benham, Spring, TX (US);
Donald A. Stern, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 13/093,244

(22) Filed: Apr. 25, 2011

(65) Prior Publication Data

US 2011/0201766 A1   Aug. 18, 2011

Related U.S. Application Data

(62) Division of application No. 10/978,792, filed on Nov. 1, 2004, now Pat. No. 7,951,889.

(60) Provisional application No. 60/516,501, filed on Oct. 31, 2003.

(51) Int. Cl.
| | |
|---|---|
| C08F 4/52 | (2006.01) |
| C08F 4/00 | (2006.01) |
| C08F 2/00 | (2006.01) |
| C08F 10/00 | (2006.01) |
| C08F 210/00 | (2006.01) |
| C08F 10/04 | (2006.01) |

(52) U.S. Cl. ........ 526/189; 526/204; 526/237; 526/290; 526/348.6; 526/348.7; 526/348

(58) Field of Classification Search ................. 526/189, 526/204, 237, 290, 348.6, 348.7, 348
See application file for complete search history.

(56) References Cited

U.S. PATENT DOCUMENTS 2,405,950 A    8/1946   Hanford
(Continued)

FOREIGN PATENT DOCUMENTS

EP             0088453 A1    9/1993
(Continued)

OTHER PUBLICATIONS

Derwent, "Solid catalyst based chemical reactor for immiscible liquids- and ultrasonic or pump based reaction of (partially) immiscible liquids," IT 1156302 B, Consiglio Naz Delle Ricerche, 1 page, Feb. 4, 1987.

(Continued)

*Primary Examiner* — William Cheung
(74) *Attorney, Agent, or Firm* — Conley Rose, P.C.; Rodney B. Carroll; Lynda S. Jolly

(57) ABSTRACT

In an embodiment, a method is disclosed to increase the activity of an ionic liquid catalyst comprising emulsifying the ionic liquid catalyst with one or more liquid components. In an embodiment, a method is disclosed comprising introducing into a reaction zone a monomer feed and a reduced amount of ionic liquid catalyst and controlling an amount of shear present in the reaction zone to maintain a desired conversion reaction of the monomer. In an embodiment, a catalyzed reaction system is disclosed comprising a reactor configured to receive one or more liquid components and ionic liquid catalyst; a device coupled to the reactor for adding high shear to the liquid components and ionic liquid catalyst; and a controller coupled to the device for adding high shear and configured to control the amount of shear added to a catalyzed reaction zone to maintain a conversion reaction.

36 Claims, 1 Drawing Sheet

U.S. PATENT DOCUMENTS

| | | | |
|---|---|---|---|
| 3,647,912 | A | 3/1972 | Langer, Jr. |
| 4,827,064 | A | 5/1989 | Wu |
| 5,087,782 | A | 2/1992 | Pelrine |
| 5,196,574 | A | 3/1993 | Kocal |
| 5,304,615 | A * | 4/1994 | Ambler et al. ............. 526/189 |
| 5,386,072 | A | 1/1995 | Cozzi et al. |
| 5,502,018 | A | 3/1996 | Chauvin et al. |
| 5,550,304 | A | 8/1996 | Chauvin et al. |
| 5,573,657 | A | 11/1996 | Degnan et al. |
| 5,731,101 | A | 3/1998 | Sherif et al. |
| 5,824,832 | A | 10/1998 | Sherif et al. |
| 5,891,830 | A | 4/1999 | Koltermann et al. |
| 6,087,307 | A | 7/2000 | Kaminski et al. |
| 6,107,374 | A | 8/2000 | Stevens et al. |
| 6,284,937 | B1 | 9/2001 | Olivier et al. |
| 6,395,948 | B1 | 5/2002 | Hope et al. |
| 6,414,099 | B1 | 7/2002 | Hlatky et al. |
| 6,444,866 | B1 | 9/2002 | Commereuc et al. |
| 6,608,149 | B2 | 8/2003 | Mawson et al. |
| 6,841,711 | B2 | 1/2005 | Krug et al. |
| 6,916,892 | B2 | 7/2005 | Tharappel et al. |
| 6,984,605 | B2 | 1/2006 | Hope et al. |
| 7,001,504 | B2 | 2/2006 | Schoonover |
| 7,259,284 | B2 | 8/2007 | Hope et al. |
| 7,309,805 | B2 | 12/2007 | Hope et al. |
| 7,351,780 | B2 | 4/2008 | Hope et al. |
| 7,615,598 | B2 | 11/2009 | Hope et al. |
| 7,951,889 | B2 | 5/2011 | Bergman et al. |
| 2002/0128532 | A1 | 9/2002 | Hope et al. |

FOREIGN PATENT DOCUMENTS

| | | |
|---|---|---|
| EP | 0791643 A1 | 8/1997 |
| EP | 1191090 A2 | 3/2002 |
| WO | 8806576 A1 | 9/1988 |
| WO | 9521871 A1 | 8/1995 |
| WO | 9521872 A1 | 8/1995 |
| WO | 9850153 A1 | 11/1998 |
| WO | 9938938 A1 | 8/1999 |
| WO | 0032658 A1 | 6/2000 |
| WO | 0041809 A1 | 7/2000 |
| WO | 0164622 A2 | 9/2001 |
| WO | 0164622 A3 | 9/2001 |
| WO | 03089390 A2 | 10/2003 |
| WO | 03089390 A3 | 10/2003 |

OTHER PUBLICATIONS

Foreign communication from a related counterpart application—International Search Report, PCT/US 03/04838, Jun. 12, 2003, 4 pages.

Foreign communication from a related counterpart application—International Search Report, PCT/US 03/12823, Dec. 17, 2003, 5 pages.

Foreign communication from a related counterpart application—International Search Report, PCT/US 03/12821, Jan. 29, 2004, 7 pages.

Foreign communication from a related counterpart application—Written Opinion of the International Preliminary Examining Authority, PCT/US 03/12821, Feb. 18, 2004, 6 pages.

Foreign communication from a related counterpart application—Written Opinion of the International Preliminary Examining Authority, PCT/US 03/04838, Apr. 8, 2004, 6 pages.

Foreign communication from a related counterpart application—Written Opinion of the International Preliminary Examining Authority, PCT/US 03/12823, Jul. 26, 2004, 6 pages.

Foreign communication from a related counterpart application—International Preliminary Examination Report, PCT/US03/12821, Sep. 7, 2004, 6 pages.

Foreign communication from a related counterpart application—International Search Report and Written Opinion, PCT/US2004/036410, Feb. 21, 2005, 7 pages.

Foreign communication from a related counterpart application—International Search Report and Written Opinion, PCT/US2004/036188, Feb. 23, 2005, 9 pages.

Foreign communication from a related counterpart application—Office Action, JP 2006-538372, Oct. 19, 2010, 4 pages.

Foreign communication from a related counterpart application—Office Action, AU 2004285044, May 12, 2009, 2 pages.

Foreign communication from a related counterpart application—Office Action, EP 04800499.8, Feb. 18, 2009, 3 pages.

Foreign communication from a related counterpart application—Office Action, SG 200602909-4, Apr. 5, 2010, 9 pages.

Foreign communication from a related counterpart application—International Preliminary Report on Patentability, PCT/US2004/036188, May 11, 2006, 7 pages.

Office Action dated Mar. 31, 2003 (9 pages), U.S. Appl. No. 10/078,759, filed Feb. 19, 2002.

Office Action (Final) dated Jan. 27, 2004 (7 pages), U.S. Appl. No. 10/078,759, filed Feb. 19, 2002.

Wasserscheid, Peter, et al., "Ionic liquids—new 'solutions' for transition metal catalysis," Angew. Chem. Int. Edition, 2000, pp. 3773-3789 plus 1 cover page, vol. 39, XP-002218385, WILEY-VCH Verlag GmbH, Weinheim, (2000).

Wolfson, Adi, et al., "Aerobic oxidation of alcohols with ruthenium catalysts in ionic liquids," Tetrahedron Letters, 2002, pp. 8107-8110, vol. 43, Elsevier Science Ltd., (2002).

* cited by examiner

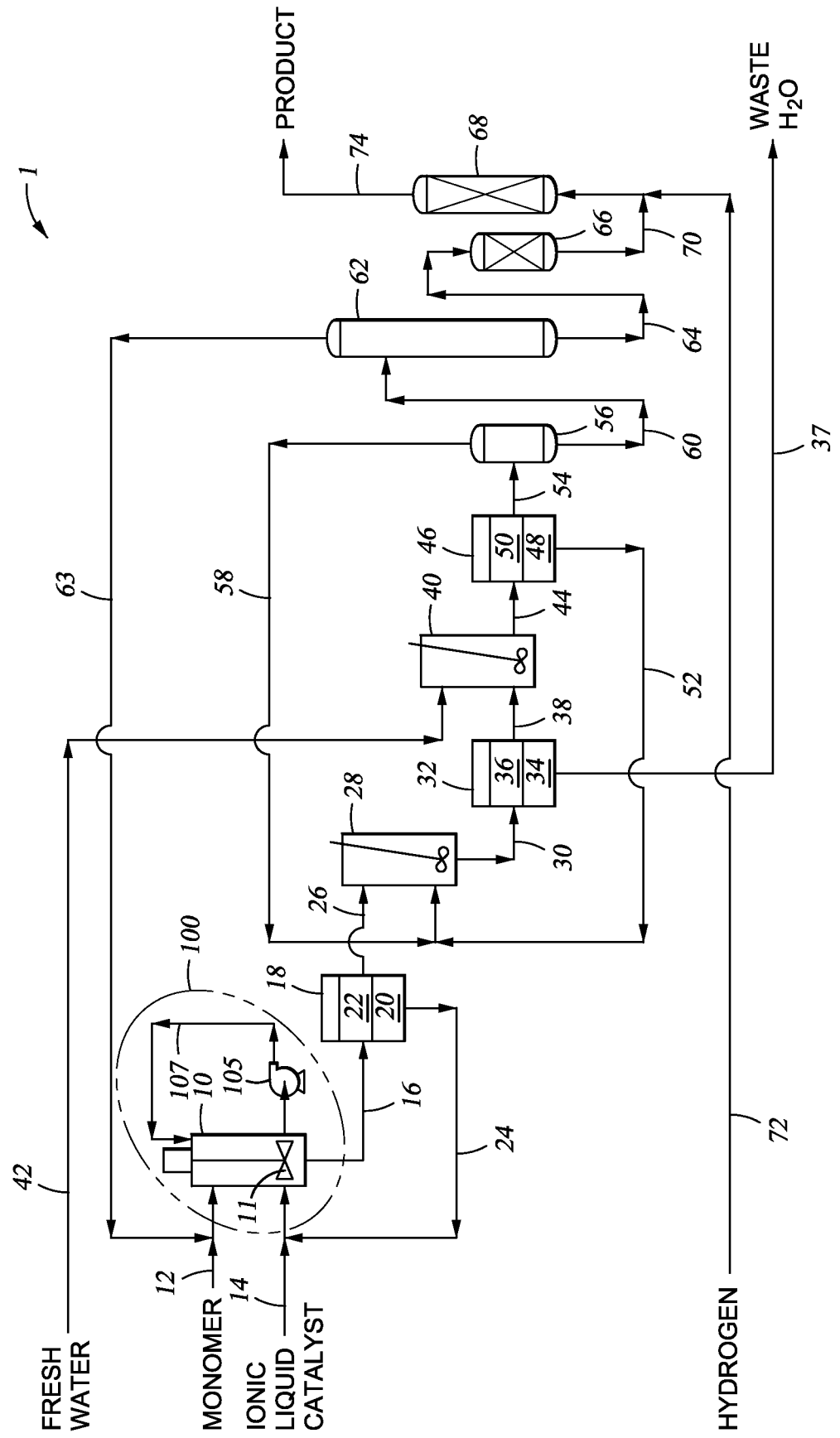

METHOD AND SYSTEM TO ADD HIGH SHEAR TO IMPROVE AN IONIC LIQUID CATALYZED CHEMICAL REACTION

CROSS-REFERENCE TO RELATED APPLICATIONS

This is a Divisional Application of U.S. patent application Ser. No. 10/978,792 filed Nov. 1, 2004, published as U.S. 2005/0119423 A1, now U.S. Pat. No. 7,951,889, which claims the benefit of and priority to provisional U.S. Patent Application No. 60/516,501, filed Oct. 31, 2003, both entitled "Method and System to Add High Shear to Improve an Ionic Liquid Catalyzed Chemical Reaction." This application is related to U.S. patent application Ser. No. 10/420,261, filed Apr. 22, 2003, now U.S. Pat. No. 7,351,780, which claims the benefit of and priority to provisional U.S. Patent Application No. 60/374,528, filed Apr. 22, 2002, both entitled "Method for Manufacturing High Viscosity Polyalphaolefins Using Ionic Liquid Catalysts." This application is also related to U.S. patent application Ser. No. 10/420,182, filed Apr. 22, 2003, now U.S. Pat. No. 6,984,605, which claims the benefit of and priority to provisional U.S. Patent Application No. 60/374,529, filed Apr. 22, 2003, both entitled "Method for Manufacturing Ionic Liquid Catalysts." This application is also related to U.S. patent application Ser. No. 10/978,547, filed Nov. 1, 2004, now U.S. Pat. No. 7,309,805, which claims the benefit of and priority to provisional U.S. Patent Application No. 60/516,516, filed Oct. 31, 2003, both entitled "Method and System to Contact an Ionic Liquid Catalyst with Oxygen to Improve a Chemical Reaction." Each of the above-listed patents or patent application is hereby incorporated herein by reference in its entirety for all purposes.

FIELD OF THE INVENTION

The present invention generally relates to ionic liquid catalytic systems for chemical conversions. More specifically, the invention relates to increased activity of ionic liquid catalysts for increased monomer conversion in the manufacture of polyalphaolefin products.

BACKGROUND

Ionic liquid catalysts may be used to catalyze a variety of chemical reactions, for example the oligomerization of alpha olefins to produce polyalphaolefins (PAO). A polyalphaolefin is a synthetic hydrocarbon liquid that is typically manufactured from the oligomerization of $C_6$ to $C_{20}$ alpha olefins. Polyalphaolefins are used in various industries as lubricants in gear oils, greases, engine oils, fiber optic gels, transmission oils, and various other lubricant applications. Ionic liquid catalysts used to produce PAO can be quite costly. Therefore, there is a need in the art for a method to increase the activity of an ionic liquid catalyst, for example to reduce the amount of required catalyst and still maintain the desired conversion, thereby improving economics of a process.

SUMMARY OF THE INVENTION

In an embodiment, a method is disclosed to increase the activity of an ionic liquid catalyst comprising emulsifying the ionic liquid catalyst with one or more liquid components. In an embodiment, a method is disclosed comprising introducing into a reaction zone a monomer feed and a reduced amount of ionic liquid catalyst and controlling an amount of shear present in the reaction zone to maintain a desired conversion reaction of the monomer. In an embodiment, a catalyzed reaction system is disclosed comprising a reactor configured to receive one or more liquid components and ionic liquid catalyst; a device coupled to the reactor for adding high shear to the liquid components and ionic liquid catalyst; and a controller coupled to the device for adding high shear and configured to control the amount of shear added to a catalyzed reaction zone to maintain a conversion reaction.

BRIEF SUMMARY OF THE DRAWINGS

FIG. 1 is a process flow schematic of one embodiment of the system to add high shear mixing to an ionic liquid catalyzed reaction incorporated within a process for manufacturing a polyalphaolefin product.

DETAILED DESCRIPTION

The invention relates to a system and or method to add high shear mixing to an ionic liquid catalyzed reaction for emulsifying the ionic liquid catalyst with one or more liquid components to increase the activity of the ionic liquid catalyst within a production process. The one or more liquid components in which the ionic liquid may be emulsified may include one or more reactants, one or more process solvents (if any), or both. In an embodiment, the one or more liquid components form a continuous phase of an emulsion and the ionic liquid catalyst forms a discontinuous phase of the emulsion. Generally, the invention may be applied to any reaction in which the size of the immiscible ionic liquid droplet can impact reaction rate, conversion percentage, catalyst activity, properties of the reaction product, or any combination of these factors. Contacting oxygen with an ionic liquid droplet in the manufacture of polyalphaolefins is a process that may impact one or more of these factors. In addition, in an olefin oligomerization reaction, the size of the ionic liquid droplet can impact one or more of these factors. Another process in which the size of the ionic liquid droplet can impact one or more of these factors is an alkylation reaction.

The invention also relates to a process to produce polyalphaolefins comprising: 1) contacting a monomer feedstock with an ionic liquid catalyst; 2) emulsifying the ionic liquid catalyst; and 3) recovering a polyalphaolefin product. In addition, the invention relates to a process to produce polyalphaolefins comprising: 1) contacting a monomer feedstock with an ionic liquid catalyst; 2) controlling an ionic liquid catalyst droplet size; and 3) recovering a polyalphaolefin product. The monomer feed, ionic liquid catalyst, methods of emulsifying the ionic liquid catalyst, methods of controlling the ionic liquid catalyst droplet size, the ionic liquid droplet size, and other process parameters are described herein. In some embodiments of such a polyalphaolefin process, the ionic liquid catalyst is contacted with oxygen. In other embodiments, the ionic liquid catalyst is contacted with water. In yet other embodiments, the ionic liquid catalyst is contacted with oxygen and water. The monomer feedstock, ionic liquid catalyst, quantity of oxygen and/or water, and other process parameters are described herein.

The following disclosure primarily focuses on the implementation of the invention to the production of PAOs. However, it should be understood that the scope of the present invention is defined by the claims and not limited to a particular embodiment described herein. Thus, the invention described herein may be equally applied to an alkylation reaction, an olefin polymerization reaction, or an olefin oligomerization reaction, for example.

FIG. 1 depicts a system 100 to add high shear mixing to an ionic liquid catalyzed process 1 for manufacturing a hydrogenated polyalphaolefin (PAO) product. The system 100 comprises a reactor 10, and liquid reactant feed stream 12 and ionic liquid catalyst stream 14 are fed into a reaction zone within the reactor. The reactor 10 may be any means known in the art for contacting the reactants with the ionic liquid under conditions described herein. Examples of suitable reactors include stirred tank reactors, which may be either a batch reactor or continuous stirred tank reactor (CSTR). Alternatively, tubular or loop reactors may be employed and equipped with suitable means for emulsifying as described herein. A reaction effluent comprising one or more reaction products may be withdrawn from reactor 10 via product line 16.

The reaction that occurs within the reaction zone may be an oligomerization reaction. In an embodiment, the reaction zone of system 100 comprises an oligomerization reaction in reactor 10 wherein reactant feed stream 12 comprises alpha-olefin monomer and product line 16 comprises a polyalphaolefin (PAO) product. Non-limiting examples of suitable alpha olefin monomers include alpha olefins having 4 to 20 carbon atoms, alternatively 6 to 20 carbon atoms, alternatively 8 to 16 carbon atoms, and alternatively 10 to 14 carbon atoms.

The reactants and ionic liquid catalyst can be introduced separately into the reaction zone via separate feed streams, as shown in FIG. 1, or they can be introduced together as a premixed mixture. Liquid components within the reaction zone include the liquid reactants such as monomer, reaction products (e.g., PAO, dimer, etc.), and optionally one or more solvents. The reactants and the ionic liquid catalyst are generally immiscible fluids, such that if simply poured together, they would form two layers of material with the more dense of the two (typically the catalyst) settling on the bottom. The amount of contact between the reactants and catalyst would be severely limited in this scenario to merely the interface between the two layers. Therefore the reactor 10 may be equipped with one or more means for emulsifying the liquid components and ionic liquid catalyst. Generally, emulsifying reduces an ionic liquid catalyst droplet size, thereby increasing a surface area of the ionic liquid catalyst available for contact in the reaction zone.

As used herein, an emulsion is a dispersion of immiscible compounds comprising an ionic liquid catalyst and one or more liquid components. Emulsifying is the process for creating an emulsion. Typically, the ionic liquid catalyst is dispersed as droplets in a continuous phase formed by the liquid components in the reaction zone such as reactants (e.g., monomer), reaction product (e.g., PAO, dimer, etc.), solvent (if present), or combinations thereof. In an embodiment, the ionic liquid catalyst is dispersed as droplets in a continuous phase comprising monomer and PAO, alternatively comprising substantially monomer and PAO, alternatively comprising substantially monomer. In an embodiment, emulsification may occur by adding mechanical energy to the ionic liquid catalyst with the one or more liquid components and can be provided, for example, by high shear mixing. Emulsification as described herein, can occur either prior to a reaction zone, (e.g., in a combined feed stream), within a reaction zone, (e.g., in a reactor), external to a reaction zone, (e.g., in a circulation loop external to a reaction zone), or by any combination thereof.

In some embodiments, the emulsifying of the ionic liquid catalyst occurs in the reactor. In other embodiments, the emulsifying of the ionic liquid catalyst occurs by adding mechanical energy to the ionic liquid catalyst with one or more liquid components. In yet other embodiments, the emulsifying of the ionic liquid catalyst occurs in a circulation loop external to the reaction zone. Means for emulsifying reactants and ionic liquid catalyst include, for example, in-line mixers such as an in-line high shear pump, an ultrasonic pump, a static mixer, or any combination of these, which could be placed in a combined reactant/ionic liquid catalyst feed line to a reactor and/or in a circulation loop connected to a reactor. Means for emulsifying reactants and ionic liquid catalyst further include one or more mixers or motorized stirrers disposed within the reactor, such as the stirrer 11 shown in FIG. 1. The stirrer could comprise a rotating impeller, a stator/rotor, or any combination thereof. In an embodiment, the stirrer 11 is a component of a CSTR, wherein the stirrer provides sufficient shear to create a desired emulsion. In line-mixers may be used in combination with mixers disposed within the reactor, for example a combination of an in-line mixer disposed in circulation loop 107 and a stirrer 11 disposed in reactor 10.

In an embodiment, a high shear pump creates the desired emulsion, for example an in-line high shear pump 105 disposed in circulation loop 107 of reactor 10. The pump 105 may be further coupled to a controller (not shown) and configured to control the amount of shear applied to reactants and catalyst in a reaction zone to maintain a conversion reaction of the reactants. In an alternative embodiment, a high shear pump is disposed in a combined reactant/ionic liquid catalyst feed stream. In an embodiment, high shear pump 105 is an in-line shear pump model No. 600LSH available from Silverson Machines, having a tip speed of 5652 ft/min at 3600 rpm and 400 gpm, with an average shear rate as provided by Silverson of 135,000 $sec^{-1}$. In the Silverson 600LSH shear pump, the components to be mixed enter the pump through a stationary cover stator inlet port and proceed into a counter-clockwise rotating inner rotor. The pump provides intense hydraulic shear (intricate mixing) as the materials are forced through a fine mesh screen (perforations in the stator) that is rotating at a high velocity before exiting through a body discharge port. Other pumps providing equivalent, high shear mixing may be employed in the process. Alternatively, an ultrasonic pump, such as the Vniitvch ultrasonic pump or the in-line Sonolator™ made by Sonic Corporation, could be used to provide the in-line high shear mixing.

High shear mixing (sometimes referred to as high shear blending) is a term of art within the mixing industry, and is used as such herein. In terms of mechanism, shear mixing is sometimes referred to as a tangential stress caused by the fluid viscosity pushing in parallel against another material surface in a tangential direction of local motion. In an embodiment, high shear is defined as having a shear rate of $\geq$ about 200 $sec^{-1}$, alternatively $\geq$ about 500 $sec^{-1}$, alternatively $\geq$ about 1000 $sec^{-1}$, alternatively $\geq$ about 5000 $sec^{-1}$, alternatively $\geq$ about 9000 $sec^{-1}$, alternatively $\geq$ about 10,000 $sec^{-1}$, alternatively $\geq$ about 20,000 $sec^{-1}$, alternatively $\geq$ about 35,000 $sec^{-1}$, alternatively $\geq$ about 50,000 $sec^{-1}$, and alternatively $\geq$ about 100,000 $sec^{-1}$, where shear rate is calculated as set forth in the examples.

In an embodiment, the droplets of ionic liquid catalyst can be larger than colloidal size. Typically the ionic liquid catalyst droplet will have a distribution of sizes. It has been discovered that the distribution of ionic liquid catalyst droplet sizes can impact the reaction described herein. In particular, it has been discovered that the relative percentage of ionic liquid catalyst droplets less than or equal to 100 microns in diameter, as measured by transmitted light microscopy, impact the ionic liquid catalyzed reactions described herein. In an embodiment, greater than 65 percent by number of the ionic liquid catalyst droplets are less than or equal to 100 microns in diameter. In other embodiments, greater than 75 percent by number of the ionic liquid catalyst droplets are less than or equal to 100 microns in diameter; alternatively, greater than 85 percent by number of the ionic liquid catalyst droplets are less than or equal to 100 microns in diameter; greater than 90 percent by number of the ionic liquid catalyst droplets are less than or equal to 100 microns in diameter; greater than 95 percent by number of the ionic liquid catalyst droplets are less than or equal to 100 microns in diameter. In an embodiment, about 100% by number of the ionic liquid catalyst droplets are less than or equal to about 100 microns in diameter.

Process conditions and operating parameters such as shear rate, feed and catalyst amounts and types, etc. may be selected to achieve desired products and properties, for example a PAO having a certain viscosity. Furthermore, the reaction may be controlled, for example the conversion or rate of reaction, based on detecting or monitoring one or more process parameter and establishing a control loop there on. In an embodiment, the amount of shear applied to the reaction zone can be controlled with a controller (not shown in FIG. 1) to maintain a desired reaction conversion. Alternatively, the amount of shear applied to the reaction zone may be controlled to achieve a desired product distribution, for example oligomer distribution. In yet another embodiment, the amount of shear applied to the reaction zone may be controlled to achieve an optimum catalytic activity to achieve a desired product distribution. The catalyzed reaction typically is an exothermic reaction and the amount of shear may be controlled to maintain a desired reaction temperature. Alternatively, the amount of shear may be controlled to maintain a desired reaction product physical property, for example hydrogenated polyalphaolefin 100° C. kinematic viscosity. In some embodiments, the amount or shear required for a certain desired product can be determined by the temperature of the reaction zone or the delta between coolant and reactor temperatures. Typically, as the amount of shear increases, the temperature of the reaction increases. Furthermore, the amount of shear required for a certain desired product can be determined by analyzing the reaction zone product composition. Typically, as the amount of shear increases, the viscosity of the reaction product increases, and vice-versa. In an embodiment, the amount of shear is controlled such that the reaction effluent comprises PAO having properties as described herein. In an embodiment, the amount of shear is controlled such that the reaction effluent comprises PAO that may be separated and upgraded into a hydrogenated PAO product having properties as described herein. Temperature and shear may be used singularly or combined to control the viscosity of a certain desired product. Additionally or alternatively, the droplet size of the dispersed ionic liquid catalyst can be measured or detected, and the amount of shear adjusted accordingly, with increased shear providing decreased droplet size and vice versa.

In an embodiment, an amount of shear is controlled to maintain a desired reaction conversion. In this embodiment, the monomer conversion greater than 70%, alternatively greater than 75 percent, and alternatively greater than 80%.

The reaction conditions within the reaction zone are maintained so as to provide suitable reaction conditions for the oligomerization of the alphaolefin of the monomer feed to give a desired polyalphaolefin product. The reaction pressure generally can be maintained in the range of from below atmospheric upwardly to about 250 psig. Since the reaction is not significantly pressure dependent, it is most economical to operate the reactor at a low pressure, for example, from about atmospheric to about 50 psig and, alternatively, from atmospheric to 25 psig. The reaction temperature is to be maintained during the reaction so as to keep the reactants and catalyst in the liquid phase. Thus, generally, the reaction temperature range is from about 20° F. to about 200° F. In an embodiment, the reaction temperature is in the range of from about 40° F. to about 150° F., and, alternatively, from 50° F. to 110° F.

The residence time of the feed within the reaction zone has a small influence on the resultant reaction product. As used herein, the term "residence time" is defined as being the ratio of the reactor volume to the volumetric introduction rate of the feeds, both the monomer feed and the ionic liquid catalyst feed, charged to or introduced into the reaction zone defined by a reactor. The residence time is in units of time. The reactor volume and feed introduction rate are such that the residence time of the total of the monomer feed and ionic liquid catalyst feed is generally in the range upwardly to about 300 minutes, but due to the need to have sufficient residence time for the reaction to take place and to economic considerations, the residence time is more appropriately in the range of from about 1 minute to about 200 minutes. In an embodiment, the residence time is in the range of from about 2 minutes to about 120 minutes and, alternatively, from 5 minutes to 60 minutes.

The amount of oxygen, the amount of water, or both present in the reaction zone may be controlled in previously referenced U.S. patent application Ser. No. 10/978,547, filed Nov. 1, 2004, now U.S. Pat. No. 7,309,805, and entitled "Method and System to Contact an Ionic Liquid Catalyst with Oxygen to Improve a Chemical Reaction," which claims the benefit of and priority to U.S. Provisional Patent Application No. 60/516,516, filed Oct. 31, 2003 and entitled "Method and System to Contact an Ionic Liquid Catalyst with Oxygen to Improve a Chemical Reaction" and U.S. patent application Ser. No. 10/420,261, filed Apr. 22, 2003, now U.S. Pat. No. 7,351,780, which claims the benefit of and priority to provisional U.S. Patent Application No. 60/374,528, filed Apr. 22, 2002, and entitled "Method for Manufacturing High Viscosity Polyalphaolefins Using Ionic Liquid Catalysts."

The catalyst concentration in the reaction zone may be used to control certain desired physical properties of the polyalphaolefin product. In an embodiment, the weight percent of ionic liquid catalyst introduced into the reaction zone may be from about 0.1 to about 50 wt. % based on the weight of the feed to the reactor, alternatively from about 0.1 to about 25 wt. %, alternatively from about 0.1 to about 10 wt. %, alternatively from about 0.1 to about 5 wt. %, alternatively from about 1 to about 3 wt. %, alternatively from about 1.5 to about 2.5 wt. %, and alternatively from about 2.0 to about 2.5 wt. %. In an embodiment, the weight percent of ionic liquid catalyst introduced into the reaction zone is less than about 7.5 wt. % based upon the weight of the feed to the reactor. In an alternate embodiment, shear pump 105 may be operated at a high shear rate of from about 20,000 to about 60,000 sec$^{-1}$. In this embodiment, the weight percent of the ionic liquid catalyst introduced into the reaction zone can be reduced by about 20 percent, for example reduced from about 2.5 wt. % of catalyst present in the reaction zone to about 2.0 wt. %, to get an equivalent viscosity product.

In the manufacture of polyalphaolefins, the monomer feedstock that is introduced into the reaction zone of the process comprises at least one alpha olefin. In an embodiment, the monomer feed comprises, based on the weight of the monomer feed, at least about 50 weight percent alpha olefins, alternatively, at least about 60, 70, 80, 90, 95, or 99 weight percent alpha olefins. In an embodiment, the monomer feed consists essentially of alpha olefins, which should be understood to include commercially available alpha olefin products. The alpha olefins and combinations thereof, which are also known as 1-olefins or 1-alkenes, suitable for use as the monomer feed of the process can have from 4 to 20 carbon atoms and include, for example, 1-butene, 1-pentene, 1-hexene, 1-octene, 1-decene, 1-dodecene, 1-tetradecene and combinations thereof. In some embodiments, the monomer feed comprises 1-decene. In other embodiments the monomer feed comprises 1-dodecene. In other embodiments, the monomer feed consists essentially of 1-decene, 1-dodecene, or mixture thereof. In an embodiment, the alpha olefins of the monomer feed have from 4 to 20 carbon atoms or mixtures thereof, alternatively from 6 to 18 carbon atoms, and alternatively from about 10 to about 12 carbon atoms.

The reactor effluent withdrawn from the reaction zone generally comprises polyalphaolefins and the ionic liquid catalyst. A variety of polyalphaolefins can be produced according to the present disclosure. Polyalphaolefins are synthetic hydrocarbon liquids manufactured from monomers. Polyalphaolefins have a complex branched structure with an olefin bond, i.e., carbon-carbon double bond that may be located anywhere along the molecule due to isomerization by the catalyst. As used herein, the term "polyalphaolefins" includes an alpha olefin oligomerization product that is either a dimer, a trimer, a tetramer, higher oligomers, a polymer of an alpha olefin, or a mixture of any one or more thereof, each of which has certain desired physical properties and, in particular, having the desired high viscosity properties all of which are more fully described below. Thus, the polyalphaolefins can include dimers, trimers, tetramers, higher oligomers, polymers, or mixture of any one or more thereof of the alpha olefin contained in the monomer feed. Such dimers, trimers, tetramers, higher oligomers, polymers, or mixture of any one or more thereof may comprise molecules having from 12 to over 1300 carbon atoms.

The reactor effluent can further comprise a dimer of the alpha olefin in the monomer feed and the unreacted monomer, if any. The polyalphaolefins can be separated from the other components of the reactor effluent including the ionic liquid catalyst, and, optionally, the unreacted monomer and dimers formed during the reaction of the monomer feed. The separated polyalphaolefins may undergo subsequent processing or upgrading such as hydrogenation to form a more stable polyalphaolefin product (referred to herein as a hydrogenated polyalphaolefin product), for example useful as a base oil stock. Hydrogenated polyalphaolefin products have olefin-carbons saturated with hydrogen, which lends excellent thermal stability to the molecule.

In an embodiment, the hydrogenated polyalphaolefin product has a viscosity of from about 2 to about 100 cSt @ 100° C., e.g., a low viscosity hydrogenated polyalphaolefin product having a viscosity of from about 2 to about 12 cSt @ 100° C., a medium viscosity hydrogenated polyalphaolefin product having a viscosity of from about 12 to about 40 cSt @ 100° C., or a high viscosity hydrogenated polyalphaolefin product having a viscosity of from about 40 to about 100 cSt @ 100° C. The weight average molecular weight of a hydrogenated polyalphaolefin product can be in the range of from about 170 to about 18,200, alternatively, from about 200 to about 10,000, alternatively from about 210 to about 8,000, alternatively from about 250 to about 3,000. In other embodiments, the weight average molecular weight of a hydrogenated polyalphaolefin product can be in the range of from about 500 to about 8,000; alternatively, from about 1,000 to about 5,000; and alternatively, from about 1,500 to 2,500.

In an embodiment, a hydrogenated polyalphaolefin product may be manufactured from either a 1-decene or 1-dodecene feedstock or mixtures thereof. The hydrogenated polyalphaolefin products from these feedstocks are especially significant in that they have unique physical properties. Typical ranges for the various physical properties of a hydrogenated polyalphaolefin product and the relevant test methods for determining the physical properties are presented in the following Table 1.

TABLE 1

Hydrogenated PAO Product Physical Properties

| Test | Units | Test Method | Value | |
|---|---|---|---|---|
| Kinematic Viscosity at 100° C. | cSt | ASTM D445 | Min | 12.0 |
| | | | Max | 35.0 |
| Bromine Index | mg/100 g | ASTM D2710 | Max | 800 |
| Volatility, Noack | wt % | CEC L40 T87 | Max | 2.0 |
| Flash Point | ° C. | ASTM D92 | Min | 245 |
| Fire Point | ° C. | ASTM D92 | Min | 290 |
| Pour Point | ° C. | ASTM D97 | Max | −30 |
| Polydispersity Index | | | Max | 3.5 |
| | | | Min | 1.0 |
| Weight Average Molecular Weight | | | Min | 170 |
| | | | Max | 18200 |

Any ionic liquid catalyst suitable to catalyze a desired chemical reaction may be used. Examples of ionic liquid compositions suitable for use in the inventive process are complexes of two components that form compositions that are liquid under the reaction conditions of the inventive process. Specifically, the ionic liquid catalyst is the complex resulting from the combination of a metal halide and an alkyl-containing amine hydrohalide salt. Such compositions are described in detail in U.S. Pat. Nos. 5,731,101 and 6,395,948, the disclosure of each of which is incorporated herein by reference in its entirety. It has been found that the use of such ionic liquid compositions provide for a polyalphaolefin end-products having certain desirable and novel physical properties that make them especially useful in various lubricant or lubricant additive applications. The use of ionic liquid composition to produce polyalphaolefin end-product are described in U.S. Pat. Nos. 6,395,948 and 7,259,284, the disclosure of each of which is incorporated herein by reference in its entirety.

The metal halides that can be used to form the ionic liquid catalyst used in this invention are those compounds which can form ionic liquid complexes that are in liquid form at the reaction temperatures noted above when combined with an alkyl-containing amine hydrohalide salt. Examples of suitable metal halides are covalently bonded metal halides. Possible suitable metals which can be selected for use herein include those from Groups IVB, VIII, IB, IIB, and IIIA of the Periodic Table of the Elements, CAS version. More specifically, the metal of the metal halides can be selected from the group consisting of aluminum, gallium, iron, copper, zinc, titanium, and indium, alternatively, the group consisting of aluminum and gallium, and alternatively, aluminum. Examples of metal halides include those selected from the group consisting of aluminum halide, alkyl aluminum halide, gallium halide, and alkyl gallium halide, titanium halide, alkyl titanium halide, mixtures thereof of which, especially desired are aluminum halide or alkyl aluminum halide. In an embodiment, the metal halide is aluminum trichloride.

The alkyl-containing amine hydrohalide salts that can be used to form the ionic liquid catalyst used in this invention include monoamines, diamines, triamines and cyclic amines, all of which include one or more alkyl group and a hydrohalide anion. The term alkyl is intended to cover straight and branched alkyl groups having from 1 to 9 carbon atoms. Examples of alkyl-containing amine hydrohalide salts useful in this invention have at least one alkyl substituent and can contain as many as three alkyl substituents. They are distinguishable from quaternary ammonium salts which have all four of their substituent positions occupied by hydrocarbyl groups. Examples include compounds having the generic formula $R_3N.HX$, where at least one of the "R" groups is alkyl, for example an alkyl of from one to eight carbon atoms (for example, lower alkyl of from one to four carbon atoms) and X is halogen, for example chloride. If each of the three R groups is designated $R_1$, $R_2$ and $R_3$, respectively, the following possibilities exist in certain embodiments: each of $R_1$-$R_3$ can be lower alkyl optionally interrupted with nitrogen or oxygen or substituted with aryl; $R_1$ and $R_2$ can form a ring with $R_3$ being as previously described for $R_1$; $R_2$ and $R_3$ can either be hydrogen with $R_1$ being as previously described; or $R_1$, $R_2$ and $R_3$ can form a bicyclic ring. In an embodiment, these groups are methyl or ethyl groups. In certain embodiments, the di- and tri-alkyl species can be used. In other embodiments, one or two of the R groups can be aryl. The alkyl groups, and aryl, if present, can be substituted with other groups, such as a halogen. Phenyl and benzyl are representative examples of possible aryl groups to select. However, such further substitution may undesirably increase the viscosity of the melt. Therefore, in an embodiment, the alkyl groups, and aryl, if present, be comprised of carbon and hydrogen groups, exclusively. Such short chains are desired because they form the least viscous or the most conductive melts. Mixtures of these alkyl-containing amine hydrohalide salts can be used.

In an embodiment, the alkyl containing amine hydrohalide salt are those compounds where the R groups are either hydrogen or an alkyl group having 1 to 4 carbon atoms, and the hydrohalide is hydrogen chloride, an example of which is trimethylamine hydrochloride.

The prepared ionic liquid may be stored and subsequently used as a catalyst for the reactions described herein. Once used as a catalyst, the ionic liquid may be separated and/or recovered from the reaction effluent by methods known to those skilled in the art. The separated and/or recovered ionic liquid may be recycled as use as a catalyst either alone or in combination with freshly prepared ionic liquid catalyst. In some cases, the recycled ionic liquid composition may be refortified with a quantity of metal halide, or amine hydrohalide salt.

The following description incorporates the inventive process disclosed into an embodiment shown in FIG. 1 wherein is represented the production process 1 for manufacturing a hydrogenated polyalphaolefin product. Monomer feed and the recycled monomer and dimer, which is more fully described below, are introduced or charged to reactor 10, hereinafter referred to as continuous stirred tank reaction or CSTR 10, by way of feed line 12. Makeup ionic liquid catalyst and recycled ionic liquid catalyst feed, which is more fully described below, are introduced or charged to CSTR 10 by way of catalyst feed line 14. The monomer and ionic liquid catalyst feeds are introduced into the CSTR 10, blended with stirrer 11, and circulated in circulation loop 107 around CSTR 10. Pump 105, placed within line 107, emulsifies the two immiscible fluids as the fluids are pumped through and returns the emulsion to the CSTR 10 via line 107. The reactor effluent from CSTR 10 is simultaneously with the introduction of the feeds withdrawn from CSTR 10 through line 16.

The reactor effluent is passed from CSTR 10 through line 16 to first phase separator 18 which provides means for separating the reactor effluent into an ionic liquid catalyst phase 20 and a hydrocarbon or polyalphaolefin-containing phase 22. The separated ionic liquid catalyst phase 20 is recycled by way of line 24 and combined with the makeup ionic liquid catalyst passing through line 14 and thereby is introduced into CSTR 10. The first phase separator may be any phase separator able to separate two immiscible liquid having different densities known to those skilled in the art. For example the first phase separator may be a gravity separator or a centrifugal separator.

The polyalphaolefin-containing phase 22 passes from phase separator 18 through line 26 to deactivation vessel 28 which provides means for contacting any remaining ionic liquid catalyst mixed with the polyalphaolefin-containing phase with water so as to deactivate the ionic liquid catalyst. The mixture of polyalphaolefin-containing phase, water and deactivated ionic liquid catalyst passes from deactivation vessel 28 through line 30 to second phase separator 32 which provides means for separating the waste water and catalyst phases 34 and polyalphaolefin containing phase 36. The waste water phase passes from second phase separator 32 by way of line 37.

The polyalphaolefin-containing phase 36 passes from second phase separator 32 through line 38 to water wash vessel 40 which provides means for contacting the polyalphaolefin-containing phase 36 with fresh water. The fresh water is charged to or introduced into water wash vessel 40 through line 42. The water and polyalphaolefin-containing phases pass from water wash vessel 40 through line 44 to third phase separator 46 which provides means for separating the water and the polyalphaolefin-containing phase introduced therein from water wash vessel 40 into a water phase 48 and polyalphaolefin-containing phase 50. The water phase 48 can be recycled and introduced into deactivation vessel 28 through line 52 thereby providing the deactivation wash water for use in the deactivation vessel 28.

The polyalphaolefin-containing phase 50 passes from third phase separator 46 through line 54 to water separation vessel 56, which provides means for separating water from the polyalphaolefin-containing phase 50, for example by flash separation, to provide a flash water stream and a polyalphaolefin-containing phase having a low water concentration. The flash water stream can pass from water separation vessel 56 and recycled to deactivation vessel 28 through line 58, or alternatively, the flash water stream can be disposed of as waste water via line 37. The polyalphaolefin-containing phase having a low water concentration passes from water separation vessel 56 through line 60 and is charged to separation vessel 62, which is for example an evaporator. Separation vessel 62 provides means for separating the polyalphaolefin-containing phase having a low water concentration into a first stream comprising monomer and, optionally, dimer, and a second stream comprising a polyalphaolefin product. The first stream passes from separation vessel 62 by way of line 63 and is recycled to line 12 wherein it is mixed with the monomer feed and charged to CSTR 10.

The second stream passes from separation vessel 62 through line 64 to guard vessel 66, which defines a zone containing guard bed material and provides means for removing chlorine and other possible contaminants from the second stream prior to charging it to hydrogenation reactor 68. The effluent from guard vessel 66 passes through line 70 to hydrogenation reactor 68. Hydrogenation reactor 68 provides means for reacting the polyalphaolefin product in the second stream to provide a hydrogenated polyalphaolefin product of which a substantial portion of the carbon-carbon double bonds are saturated with hydrogen. Hydrogen is introduced by way of line 72 into line 70 and mixed with the second stream prior to charging the thus-mixed hydrogen and second stream into hydrogenation reactor 68. The hydrogenated polyalphaolefin product passes from hydrogenation reactor 68 by way of line 74.

The present disclosure primarily focuses on a PAO production embodiment, but it should be understood that the scope of the present invention is defined by the claims and not limited to a particular embodiment described herein. For example, in an alternate embodiment, the reaction zone of system 100 comprises an alkylation reaction in reactor 10 wherein reactant feed stream 12 comprises an aromatic compound such as benzene, toluene, xylene, or naphthalene and product stream 16 comprises an alkylated product.

In an embodiment, the alkylation reaction may be a Friedel-Crafts alkylation. In an embodiment, the alkylation reaction is alkylation of benzene, for example according to the method and apparatus in the U.S. Pat. No. 5,824,832, entitled "Linear Alkylbenzene Formation Using Low Temperature Ionic Liquid", filed on Oct. 20, 1998, incorporated by reference herein in its entirety. In an embodiment, benzene is alkylated to form ethylbenzene, cumene, or linear alkylbenzenes (LAB). For example, benzene may be combined, typically in molar excess, with a suitable alkylating reagent having from about 2 to 54 carbon atoms such as olefins, halogenated alkanes, or mixtures thereof. Non-limiting examples of suitable halogenated alkanes include $C_4$-$C_{20}$ chloroparaffins, alternatively $C_{10}$-$C_{14}$ chloroparaffins. Non-limiting examples of suitable olefins include linear, unbranched monoolefins and mixtures thereof having 4 to 20 carbon atoms, alternatively 20 to 24 carbon atoms, alternatively 8 to 16 carbon atoms, and alternatively 10 to 14 carbon atoms, wherein the double bond may be positioned anywhere along the linear carbon chain. Non-limiting examples of other suitable alkylating agents include olefin oligomers such as propylene tetramer and unhydrogenated polyalphaolefins. Ionic liquid catalysts such as those described in more detail herein may be used to catalyze such alkylation reactions.

The following examples of the invention are presented merely for the purpose of illustration and are not intended to limit in any manner the scope of the invention.

EXAMPLES 1-3

High Shear Added in Oligomerization of 1-Decene

The following examples, examples 1-3, illustrate the effect of shear and high shear on some of the physical properties of the oligomer reaction product and the percentage of monomer converted in the reaction resulting from the continuous process for the oligomerization of 1-decene.

The shear rate data for each piece of mixing equipment used in the 3 examples was based on the fundamental calculation of velocity or tip speed divided by the distance or gap between the two surfaces. The one-gallon pilot plant reactor had an inside diameter of 5-inches. The reactor was equipped with a 2.5-inch radial six-blade impeller. A Tuthill gear pump housed two 0.5-inch diameter ten-teeth gears. A Silverson mixer (model 150L) was equipped with a 1.5-inch diameter rotor. Table 2 below contains the specific information required to calculate the basic shear rate. For example, the reactor impeller shear rate calculation was based on:

a) Circumference of impeller=pi(2.5 in)=7.854 in b) Impeller tip speed=(660 rev/min)(7.854 in/rev)/12 in/ft=432 ft/min c) Shear rate=tip speed/gap=(432 ft/min)(12 in/ft)/60 sec/min)/1.25 in=69 sec$^{-1}$

TABLE 2

|  | Diameter, in | Speed, rpm | Tip Speed, ft/min | Gap, in | Shear Rate, sec$^{-1}$ |
|---|---|---|---|---|---|
| Reactor Impeller | 2.5 | 660 | 432 | 1.25 | 69 |
| Tuthill Gear Pump | 0.5 | 1800 | 236 | 0.005 | 9440 |
| Silverson Mixer | 1.5 | 2880 | 1130 | 0.003 | 44,960 |

Example 1

In a continuous process, 1-decene was fed at a rate of 3000 grams/hour along with a catalyst feed (1.65:1 molar ratio AlCl3:TMA.HCl) of 2.5 weight % into a 1-gallon stirred-tank reactor. The reactor was equipped with external and internal cooling coils. The 1-decene feed contained 31 to 61 ppm water. The reactor level was controlled to roughly half of the volume, which gave residence times from 27 to 30 minutes. The reactor was agitated with an internal stirrer operating at 432 ft/min tip speed. The reactor stirrer was set at 660 rpm. The reaction section was controlled from 19 to 22° C. under a headspace of 21% oxygen (balance nitrogen) at a pressure of 30 psig. The reactor effluent was quenched with water to deactivate the catalyst. The resulting product was distilled to a target monomer plus dimer content of less than about 2 weight percent. Monomer conversion of the water-quenched product was determined using gas chromatography. The percent monomer conversion of the water-quenched product and the properties of the distilled product from this example and of the following examples are presented in Table 3 below.

Example 2

The conditions for Example 1 were repeated with the exception of the reactor agitation. In this example the reactor included a pump around loop with a Tuthill gear pump model no. 9174S with a tip speed of 236 ft/min. As shown below in Table 3, the increase in shear rate results in enhanced 1-decene conversion and viscosity.

Example 3

The conditions for Example 2 were repeated with the exception of the addition of a high shear mixer that was used in the pump around loop. The high shear mixer (Silverson model 150L) was equipped with a 1 horsepower motor having a 1.5-inch diameter rotor. Tip speed at 2880 rpm is 1130 ft/min. The nominal flow at 2880 rpm is 1.6 gallons per minute. The mixer had a square hole high shear screen installed, which provided an estimated shear rate in rotor/stator gap of 44,960 per sec. Stator gap is 0.003 inch. As shown below in Table 3, the increase in shear rate again results in enhanced 1-decene conversion and viscosity. The equipment listed in Table 3 is additive to each previous example.

TABLE 3

| Example | Shear Rating | Equipment | Monomer Conversion | 100° C. Viscosity cSt | 40° C. Viscosity cSt | Viscosity Index (VI) |
|---|---|---|---|---|---|---|
| 1 | 1 (lowest) | Reactor stir mechanism | 69% | 27.4 | 228.4 | 155 |
| 2 | 2 | Add gear pump | 74% | 29.2 | 220.5 | 172 |
| 3 | 3 (highest) | Add high shear mixer | 78% | 33.1 | 234.4 | 187 |

EXAMPLES 4

Catalyst Droplet Size for High Shear Oligomerization

The following example describes how samples were acquired and analyzed to determine catalyst droplet size as a function of shear. 678 grams of 1-decene and 13.5 grams of catalyst were added to a 1-gallon stirred-tank reactor. The reactor was maintained at 16.9° C. under a 15 psig nitrogen headspace. The reactor stirrer was set at 660 rpm. A first sample was pulled 20 minutes after catalyst was added. The reactor contents were then diverted through a pump-around loop, which included the gear pump described previously. This shear regime was maintained for 30 minutes. The reactor temperature increased slightly to 17.6° C. The high-shear mixer as described previously was introduced into the pump-around loop, in addition to the Tuthill gear pump, 50 minutes after initial catalyst charge. The temperature increased to 19.6° C. A second sample was pulled 20 minutes after the high-shear mixer was turned on.

Transmitted light microscopy was used to image the catalyst droplet size following low and high shear mixing. Catalyst droplets from the low shear sample were allowed to settle to the bottom of the sample vial before being collected with a pipette and transferred to a glass slide. A few drops of the high shear sample solution were placed on a glass slide. No cover slides were used on either sample. The goal was to determine the size of single droplets, not agglomerates. Table 4 below summarizes the frequency percentage of droplets within a size range for the low shear and high shear samples.

TABLE 4

| Droplet Size Range (microns) | Frequency Percentage Low Shear Sample (stirrer) | Frequency Percentage High Shear Sample (stirrer + gear pump + high-shear mixer) |
|---|---|---|
| 0-40 | 10 | 19 |
| 41-60 | 29 | 50 |
| 61-80 | 5 | 25 |
| 81-100 | 14 | 6 |
| 101-150 | 24 | 0 |
| 151-200 | 19 | 0 |

The results show that 100% of the high shear sample was composed of droplets equal to or smaller than 100 microns. By comparison, approximately 43% of the low shear sample droplets were greater than 100 microns in length.

As shown by the examples, emulsifying can reduce the ionic liquid catalyst droplet size, thereby increasing the surface area of the ionic liquid catalyst available for contact in the reaction zone. The increased surface area of the ionic liquid catalyst in the emulsion may increase the catalyst's activity by improving the conversion rate and/or improving the viscosity index (VI) of a PAO product. Alternatively stated, emulsification of the immiscible ionic liquid catalyst and reactant(s) improves the usefulness of the catalyst by reducing the amount of catalyst that may be required for achieving a certain product viscosity (i.e., the same amount of surface area available for contact can be achieved using less catalyst).

In the description above, like parts are marked throughout the specification and drawings with the same reference numerals, respectively. The drawing figures are not necessarily to scale. Certain features of the invention may be shown exaggerated in scale or in somewhat schematic form and some details of conventional elements may not be shown in the interest of clarity and conciseness. The present disclosure is susceptible to embodiments of different forms. There are shown in the drawings, and herein are described in detail, specific embodiments of the present disclosure with the understanding that the present disclosure is to be considered an exemplification of the principles of the invention, and is not intended to limit the invention to that illustrated and described herein. It is to be fully recognized that the different teachings of the embodiments discussed above may be employed separately or in any suitable combination to produce desired results. Specifically, the method and system of the present invention disclosed herein to add high shear mixing to an ionic liquid catalyzed reaction may be used with any suitable ionic liquid catalyzed reaction wherein the reaction product contains a converted chemical reactant. In a desirable embodiment, the method and system to add high shear mixing to an ionic liquid catalyzed reaction of the present disclosure is for an oligomerization reaction for producing PAO from monomer or mixtures thereof, in the presence of an ionic liquid based catalyst system and the detailed description above is focused on this embodiment but with the understanding that the present invention may have broader applications including such reactions as a Friedel-Crafts alkylation. Although only a few embodiments of the present invention have been described herein, it should be understood that the present disclosure may be embodied in many other specific forms without departing from the spirit or the scope of the present disclosure. Any examples included are to be considered as illustrative and not restrictive, and the disclosure is not to be limited to the details given herein, but may be modified within the scope of the appended claims along with their full scope of equivalents.

That which is claimed is:

1. A method to increase activity of an ionic liquid catalyst in a reaction zone comprising one or more liquid components, the method comprising:

emulsifying the ionic liquid catalyst with the one or more liquid components via shear mixing, wherein the shear mixing is at a high shear rate of greater than or equal to about 5,000 sec$^{-1}$; and controlling an amount of shear to maintain a desired reaction conversion.

2. The method of claim 1 wherein the emulsifying occurs prior to the reaction zone, within the reaction zone, external to the reaction zone, or by any combination thereof.

3. The method of claim 1 wherein the emulsifying occurs in a feed stream comprising ionic liquid catalyst and one or more reactants.

4. The method of claim 1 wherein the emulsifying occurs in a reactor.

5. The method of claim 1 wherein the emulsifying occurs in a circulation loop external to the reaction zone.

6. The method of claim 1 wherein the shear mixing is at a high shear rate of greater than or equal to about 20,000 sec$^{-1}$.

7. The method of claim 1 wherein the amount of shear is controlled to maintain a desired reaction temperature.

8. The method of claim 1 wherein the amount of shear is controlled to maintain a desired reaction product physical property.

9. The method of claim 1 wherein emulsifying reduces an ionic liquid catalyst droplet size, thereby increasing a surface area of the ionic liquid catalyst available for contact in the reaction zone.

10. The method of claim 1 wherein the reaction within the reaction zone is an alkylation reaction.

11. The method of claim 10 wherein the alkylation reaction is a Friedel-Crafts alkylation.

12. The method of claim 11 wherein the one or more liquid components comprise benzene, toluene, xylene, or naphthalene.

13. The method of claim 1 wherein the reaction within the reaction zone is a polymerization reaction.

14. The method of claim 1 wherein the reaction is an oligomerization reaction.

15. The method of claim 14 wherein the one or more liquid components comprise one or more monomers or mixtures thereof.

16. The method of claim 14 wherein a weight percent of the ionic liquid catalyst introduced present in the reaction zone is less than or equal to about 7.5 wt. %.

17. The method of claim 14 wherein a weight percent of the ionic liquid catalyst present in the reaction zone is reduced by greater than or equal to about 20 percent.

18. The method of claim 15 wherein the monomer comprises alpha olefins having from about 6 to about 20 carbon atoms or mixtures thereof.

19. The method of claim 15 wherein the monomer comprises alpha olefins having from about 10 to about 12 carbon atoms.

20. The method of claim 1 wherein the amount of shear is determined by a temperature of the reaction zone, by analyzing a polyalphaolefin product, or a combination thereof.

21. The method of claim 14 further comprising recovering a polyalphaolefin product having a viscosity of from about 2 to about 12 cSt @ 100° C.

22. The method of claim 20 further comprising recovering a polyalphaolefin product having a viscosity of from about 12 to about 40 cSt @ 100° C.

23. The method of claim 20 further comprising recovering a polyalphaolefin product having a viscosity of from about 40 to about 100 cSt @ 100° C.

24. The method of claim 1 wherein a resultant emulsion comprises ionic liquid catalyst droplets less than or equal to about 100 microns in diameter.

25. A method for oligomerizing a monomer into polyalphaolefins, comprising:
emulsifying an ionic liquid catalyst with the monomer via shear mixing, wherein the monomer comprises alpha olefins having from about 6 to about 20 carbon atoms; and
controlling an amount of shear to maintain a desired reaction conversion.

26. The method of claim 25 wherein the ionic liquid catalyst and the monomer are emulsified in a recirculation loop to a reactor.

27. The method of claim 25 wherein the ionic liquid catalyst and the monomer are emulsified by a mixer disposed in a reactor.

28. The method of claim 25 wherein a resultant emulsion comprises ionic liquid catalyst droplets less than or equal to about 100 microns in diameter dispersed in the monomer.

29. A method for oligomerizing a monomer into polyalphaolefins, comprising:
mixing an ionic liquid catalyst with the monomer under high shear, wherein the monomer comprises alpha olefins having from about 6 to about 20 carbon atoms; and
controlling an amount of shear to maintain a desired reaction conversion.

30. The method of claim 1 wherein the monomer comprises alpha olefins having from about 8 to about 16 carbon atoms.

31. The method of claim 25 wherein the monomer comprises alpha olefins having from about 8 to about 16 carbon atoms.

32. The method of claim 29 wherein the monomer comprises alpha olefins having from about 8 to about 16 carbon atoms.

33. The method of claim 25 wherein the shear mixing is at a high shear rate of greater than or equal to about 5,000 sec$^{-1}$.

34. The method of claim 25 wherein the shear mixing is at a high shear rate of greater than or equal to about 20,000 sec$^{-1}$.

35. The method of claim 29 wherein the shear mixing is at a high shear rate of greater than or equal to about 5,000 sec$^{-1}$.

36. The method of claim 29 wherein the shear mixing is at a high shear rate of greater than or equal to about 20,000 sec$^{-1}$.

* * * * *